United States Patent
Meritt

(10) Patent No.: US 10,520,377 B2
(45) Date of Patent: Dec. 31, 2019

(54) WALL SHEAR SENSORS WITH MULTIPLE BENDING BEAM FLEXURE AND MEASUREMENT SYSTEMS INCLUDING THE WALL SHEAR SENSORS

(71) Applicant: Ahmic Aerospace, LLC, Beavercreek, OH (US)

(72) Inventor: Ryan James Meritt, Beavercreek, OH (US)

(73) Assignee: Ahmic Aerospace, LLC, Beavercreek, OH (US)

( * ) Notice: Subject to any disclaimer, the term of this patent is extended or adjusted under 35 U.S.C. 154(b) by 25 days.

(21) Appl. No.: 15/722,707

(22) Filed: Oct. 2, 2017

(65) Prior Publication Data

US 2018/0094992 A1   Apr. 5, 2018

Related U.S. Application Data

(60) Provisional application No. 62/402,169, filed on Sep. 30, 2016.

(51) Int. Cl.
*G01M 5/00* (2006.01)
*G01L 1/22* (2006.01)
(Continued)

(52) U.S. Cl.
CPC .......... *G01L 1/2243* (2013.01); *B81B 3/0072* (2013.01); *G01L 5/16* (2013.01);
(Continued)

(58) Field of Classification Search
CPC ..... G01L 1/2225; G01L 1/2243; G01L 1/246; G01L 1/24; G01G 3/1412; F24F 6/02;
(Continued)

(56) References Cited

U.S. PATENT DOCUMENTS 3,439,761 A * 4/1969 Laimins ............... G01L 1/2231
177/16
3,552,199 A * 1/1971 Pugnaire et al. ........ G01G 3/00
177/211
(Continued)

OTHER PUBLICATIONS

"Direct Measurement of Skin Friction in Complex Flows", Schetz, Joseph A., 2010, American Institute of Aeronautics and Astronautics.
(Continued)

*Primary Examiner* — Brandi N Hopkins
(74) *Attorney, Agent, or Firm* — Dinsmore & Shohl, LLP

(57) ABSTRACT

A wall shear sensor includes a floating element fixedly attached to a base. The floating element has a sensing head opposite the base, and a split-beam flexure between the sensing head and the base. The wall shear sensor further includes at least one strain gauge coupled to the split-beam flexure, which measures strain imposed on walls of the split-beam flexure when a wall shear is applied across a head surface of the sensing head. The split-beam flexure has at least one channel defined through the split-beam flexure perpendicular to a first transverse axis of the floating element. The floating element sways parallel to the first transverse axis of the floating element when the wall shear is applied. Wall shear measurement systems include a test body, a sensor housing mounted to the test body, and a wall shear sensor in the sensor housing.

20 Claims, 10 Drawing Sheets

(51) Int. Cl.
　　　*G01N 19/02*　　　(2006.01)
　　　*B81B 3/00*　　　(2006.01)
　　　*G01L 5/16*　　　(2006.01)
　　　*G01N 19/08*　　　(2006.01)

(52) U.S. Cl.
　　　CPC ........ *G01M 5/0041* (2013.01); *G01M 5/0083* (2013.01); *G01N 19/02* (2013.01); *G01N 19/08* (2013.01)

(58) Field of Classification Search
　　　CPC ........ F24F 2110/00; F24F 6/025; F24F 11/30; G05D 22/02; G05D 9/12; G01B 11/165; G01B 11/18; G01D 5/353; G01N 3/24; G01N 13/00; G01N 2013/0216; G01N 2203/0623
　　　See application file for complete search history.

(56) References Cited

U.S. PATENT DOCUMENTS

| | | |
|---|---|---|
| 4,112,752 A | 9/1978 | Hafner et al. |
| 4,240,290 A | 12/1980 | Montoya et al. |
| 4,283,941 A | 8/1981 | Kutsay |
| 4,290,302 A | 9/1981 | Harris |
| 4,364,280 A | 12/1982 | Kutsay |
| 4,420,985 A * | 12/1983 | Raskin .................. G01L 1/2225 73/862.633 |
| 4,448,083 A | 5/1984 | Hayashi |
| 4,464,928 A | 8/1984 | Dealy |
| 4,485,681 A | 12/1984 | Hatamura |
| 4,573,362 A * | 3/1986 | Amlani .................. G01L 1/2218 73/862.044 |
| 4,604,903 A | 8/1986 | Tcheng et al. |
| 4,674,339 A | 6/1987 | Hatamura et al. |
| 4,836,035 A | 6/1989 | Tcheng et al. |
| 5,889,214 A | 3/1999 | Kang et al. |
| 6,225,576 B1 | 5/2001 | Poole et al. |
| 6,260,424 B1 | 7/2001 | Koelblinger |
| 6,426,796 B1 | 7/2002 | Pulliam et al. |
| 7,770,463 B2 | 8/2010 | Sheverev et al. |
| 7,784,363 B2 * | 8/2010 | Ihrke .................. B25J 13/084 73/862.041 |
| 7,921,731 B2 | 4/2011 | Bajikar et al. |
| 8,276,463 B2 | 10/2012 | Sheverev et al. |

OTHER PUBLICATIONS

"Practical Strain Gage Measurements", Agilent Technologies, 1999.

* cited by examiner

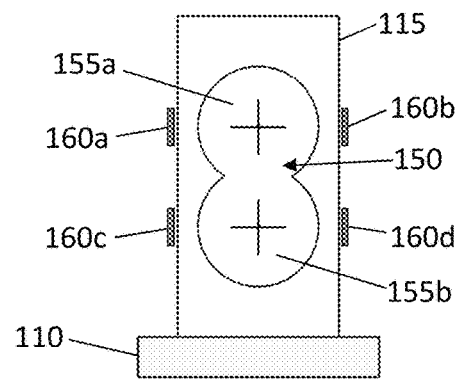
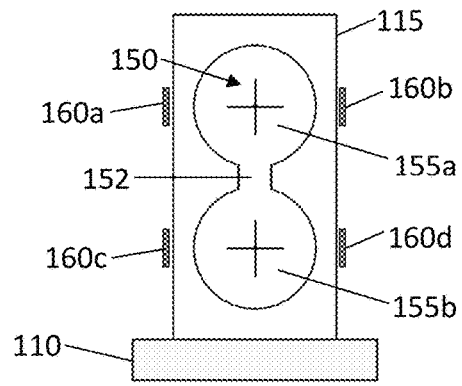
FIG. 5A  FIG. 5B
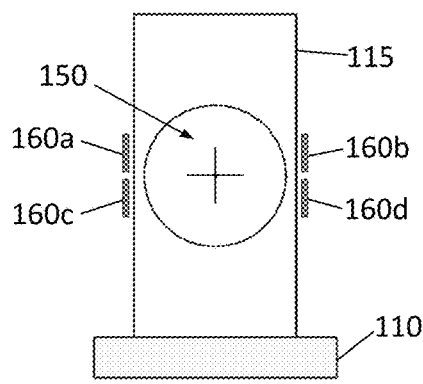
FIG. 5C
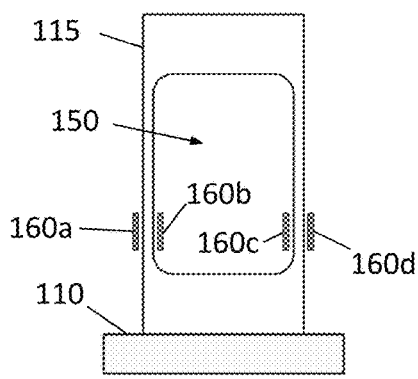
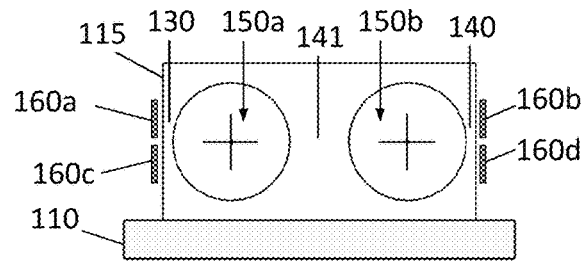
FIG. 5D  FIG. 5E

WALL SHEAR SENSORS WITH MULTIPLE BENDING BEAM FLEXURE AND MEASUREMENT SYSTEMS INCLUDING THE WALL SHEAR SENSORS

CROSS REFERENCES TO RELATED APPLICATIONS

This application claims the benefit of priority under 35 U.S.C. § 119(e) to U.S. Provisional Application Ser. No. 62/402,169, filed Sep. 30, 2016, which application is incorporated herein by reference in its entirety.

TECHNICAL FIELD

The present disclosure relates to wall shear sensors and wall shear measurement systems and, more particularly, to wall shear sensors having multiple bending beams and wall shear measurement systems incorporating the wall shear sensors.

BACKGROUND

Accurate knowledge of wall shear stress ($\tau_w$), or skin friction ($C_f$), can be a tool for assessing the performance and survivability of aerodynamic and hydrodynamic systems. Experimental wall shear is also an important measurement needed to anchor, validate, and verify analytical and computation methods including their submodels. Skin friction is often expressed as a dimensionless coefficient of wall shear stress. Skin friction drag may be determined directly or indirectly. Measurement techniques for skin friction are distinguished by their approaches and the physical quantities that they measure. Indirect methods require the properties of the flow and boundary layer to be well-defined. Through analytical correlation or analogy, shear at the wall is subsequently solved for as a function of other flowfield measurements. For example, the Reynolds Analogy is used to infer skin friction from a measurement of surface heat flux.

Although indirect techniques have been shown to work in many common, well-understood flow environments, they are not considered reliable in complex flowfields. In contrast, direct methods do not require any foreknowledge, but instead directly measure the tangential frictional forces imparted by the moving flow. Conventional wall shear sensors are capable of measuring such forces but in general suffer from decreased reliability and accuracy when the moving flow is affected by pressure gradients such as those caused by shock waves. Therefore, needs exist for reliable apparatus that can directly measure wall shear in a manner that is highly sensitive, yet with significant reduction or elimination of errors resulting from the moment caused by impinging pressure gradients or shock waves.

SUMMARY

According to embodiments described herein, a wall shear sensor includes a floating element fixedly attached to a base. The floating element has a sensing head opposite the base, and a split-beam or multiple beam flexure between the sensing head and the base. The wall shear sensor further includes at least one strain gauge coupled to the split-beam flexure. The strain gauge measures a strain imposed on a portion of the split-beam flexure when a wall shear is applied across a head surface of the sensing head. The split-beam flexure has at least one channel defined through the split-beam flexure parallel to a first transverse axis of the floating element. The floating element sways in a sway direction perpendicular to the first transverse axis of the floating element when wall shear is applied across the head surface of the sensing head.

According to further embodiments described herein, a wall shear measurement system includes a test body having a flow surface; at least one sensor housing mounted to the test body; and a wall shear sensor in the at least one sensor housing. The wall shear sensor includes a floating element fixedly attached to a base. The floating element has a sensing head opposite the base, and a split-beam or multiple beam flexure between the sensing head and the base. At least one strain gauge is coupled to the split-beam flexure. The strain gauge measures a strain imposed on the split-beam flexure when a wall shear is applied across a head surface of the sensing head. The split-beam flexure has a channel defined through the split-beam flexure parallel to a transverse axis of the split-beam flexure. The wall shear sensor sways in a sway direction perpendicular to the transverse axis of the split-beam flexure when a wall shear is applied across the head surface of the sensing head. The sensor housing laterally surrounds the floating element of the wall shear sensor. An interior space laterally surrounding the floating element is defined between the floating element and the sensor housing. The interior space includes a small gap portion laterally surrounding the sensing head of the floating element. The head surface of the sensing head is exposed outside the sensor housing.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIGS. 5A-5E are side views of illustrative channel configurations of split-beam flexures of the wall shear sensors according to embodiments described herein.

DETAILED DESCRIPTION

Embodiments of this disclosure include wall shear sensors and wall shear measurement systems including at least one wall shear sensor. The wall shear sensors include a floating element having a split-beam or multiple beam flexure. Strain measurements from various locations on the split-beam flexure may be analyzed to provide accurate direct measurements of wall shear over a head surface of the floating element. The split-beam flexure also enables accurate measurements of the wall shear, even when pressure differentials across the head surface result from natural occurrences such as shock waves. The wall shear sensors according to embodiments herein may be suitable for various applications including, but not limited to, the sensing of wall shear over a flow surface such as an aircraft or maritime vehicle.

Figure 1:
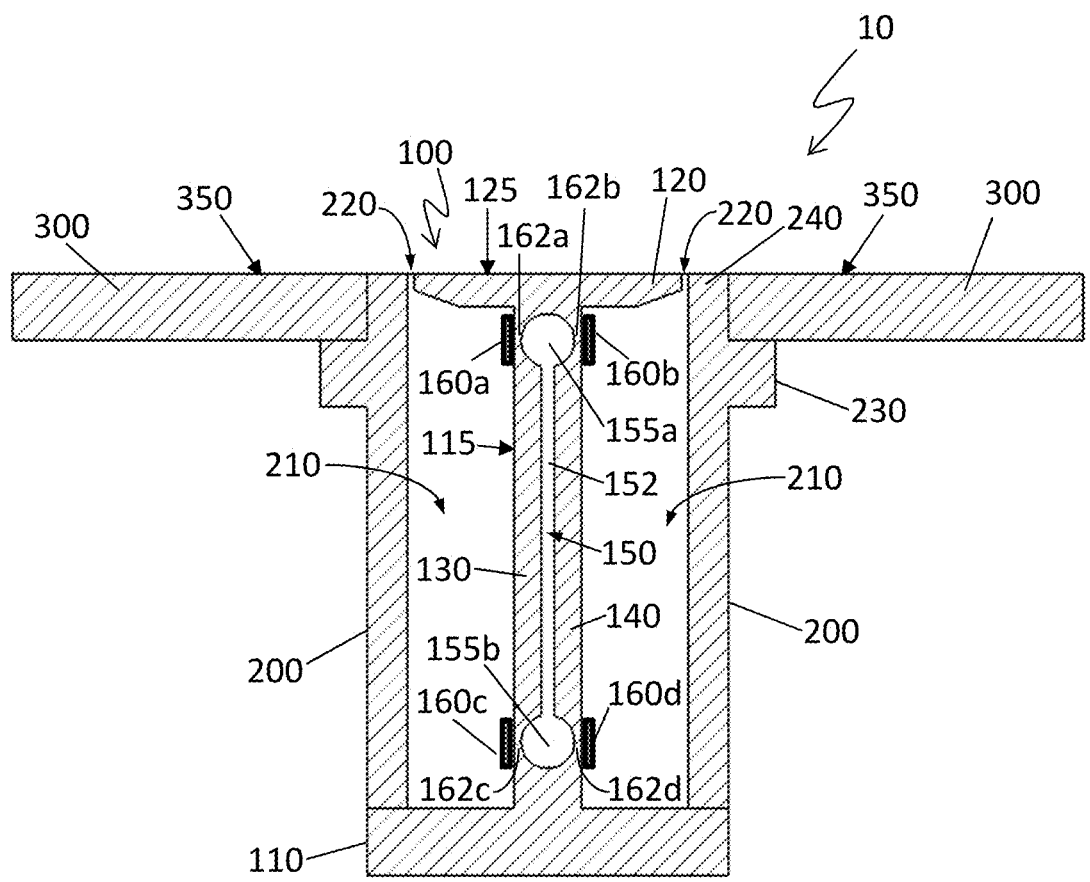
FIG. 1 is a cross-sectional side-view of a wall shear sensor according to one or more embodiments described herein.
Figure 2:
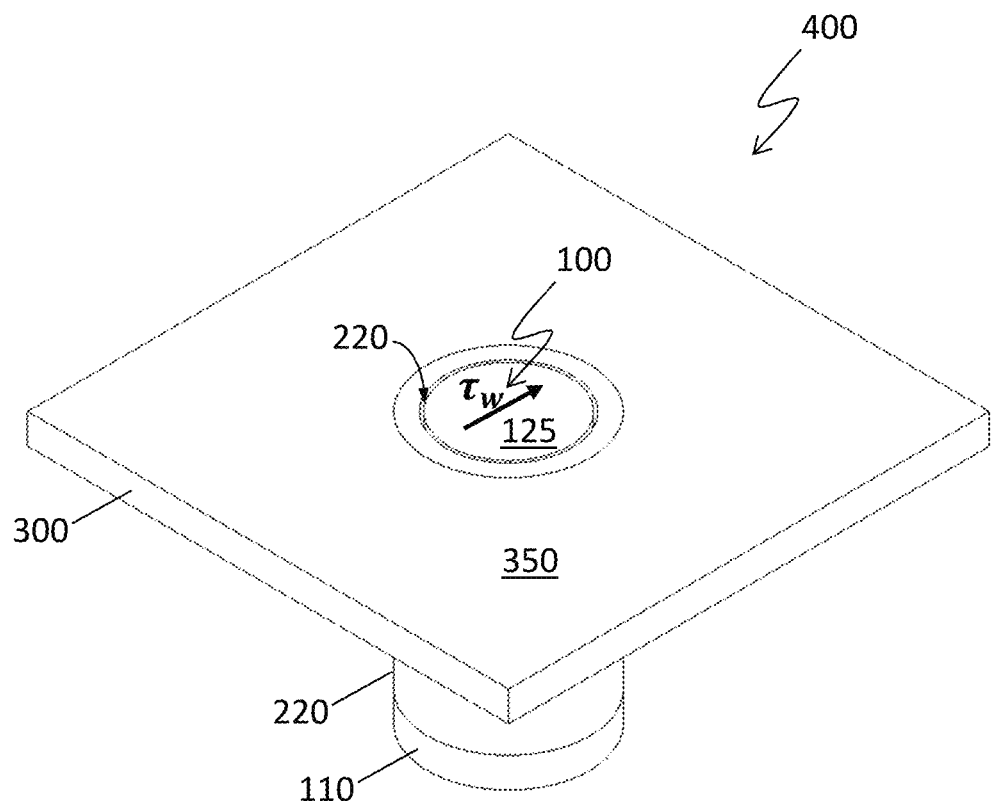
FIG. 2 is a perspective view of the wall shear sensor of FIG. 1 inside a sensor housing that is mounted to a test body having a flow surface.

Referring to FIGS. 1 and 2, a wall shear sensor 10 according to embodiments includes a floating element 100 and a plurality of strain gauges 160a, 160b, 160c, 160d coupled to the floating element 100 to measure a strain on portions of the floating element 100. In some embodiments, the floating element 100 may be disposed within a sensor housing 200 that laterally surrounds the floating element 100. When the floating element 100 is within a sensor housing 200, an interior space 210 may be defined between the floating element 100 and the sensor housing 200, thus laterally surrounding the floating element 100. The interior space 210 includes a small gap portion 220 laterally surrounding the sensing head 120 of the floating element 100. The head surface 125 of the sensing head 120 is exposed outside the sensor housing 200 to fluids such a gas flow, an air flow, or a liquid flow that pass over the head surface 125 during a wall shear measurement. In some embodiments, the wall shear sensor 10 including the floating element 100 housed within the sensor housing 200 may be mounted to a test body 300 having a flow surface 350. The mounting of the wall shear sensor 10 may be facilitated by a mounting flange 230 and a protective collar 240 of the sensor housing 200. In some embodiments, the wall shear sensor 10 is mounted to the test body 300 such that the head surface 125 of the floating element 100 is coplanar or substantially coplanar with the flow surface 350.

The head surface 125 of the floating element 100 may have any shape that enables the floating element 100 to sway or bend when a wall shear is applied across the head surface 125. In example embodiments, the head surface 125 may be shaped as a square, rectangle, circle, or an oval, for example. In some embodiments, the head surface 125 is circular. In some illustrative applications, it may be suitable for a head surface 125 that is circular to have a diameter from about 0.25 inches to about 0.75 inches. However, it should be understood that the diameter of such a head surface 125 may be substantially smaller than 0.25 inches or substantially larger than about 0.75 inches.

Figure 3:
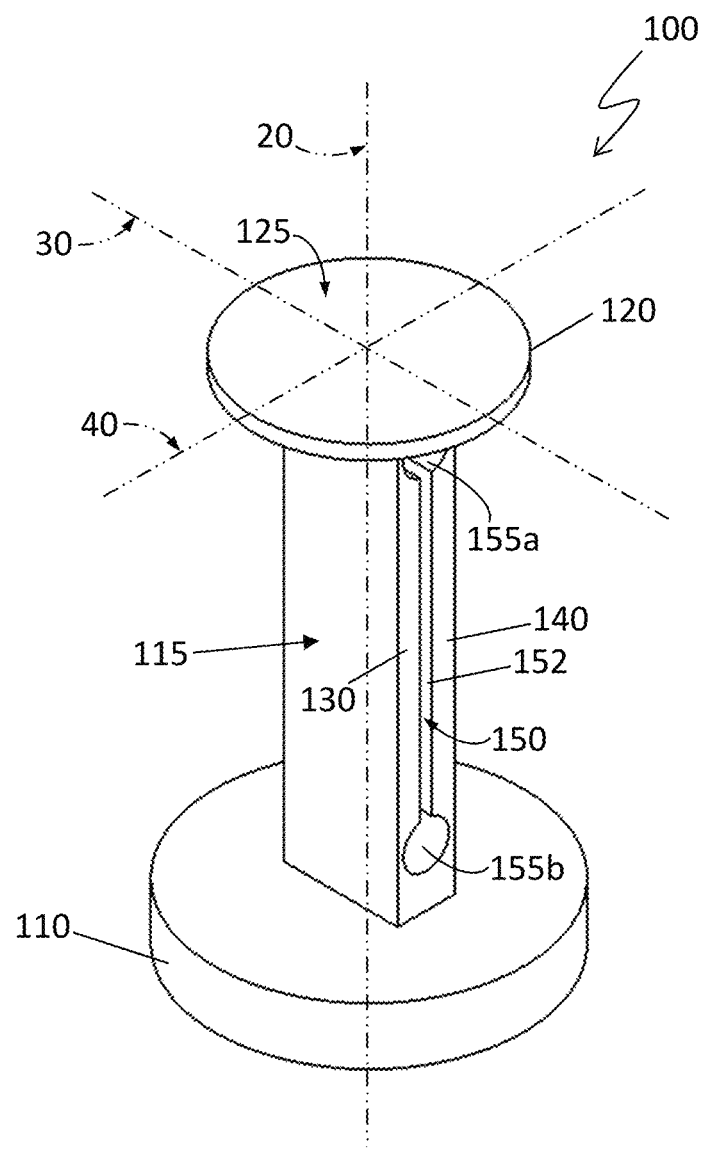
FIG. 3 is a perspective view of a floating element of a wall shear sensor according to one or more embodiments described herein.

Referring to FIG. 3, the floating element 100 is fixedly attached or mounted to a base 110. The floating element 100 and the base 110 may be a unitary component that is manufactured as a single part or may be two components that are joined together by any suitable method. A longitudinal axis 20 of the floating element 100 is defined perpendicular to the base 110 in the lengthwise direction of the floating element 100. The floating element 100 includes a sensing head 120 opposite the base 110. The sensing head 120 includes a head surface 125. The head surface 125 may be disposed within a plane perpendicular to the longitudinal axis 20 of the floating element 100.

The floating element 100 also includes a split-beam flexure 115 between the sensing head 120 and the base 110. The split-beam flexure 115 has at least one channel 150 defined through the split-beam flexure 115 parallel to a first transverse axis 30 of the split-beam flexure 115. The size and shape of the channel 150 or multiple channels in the split-beam flexure 115 may be tailored or optimized to provide desirable strain characteristics to the split-beam flexure 115 for the measurement application of the wall shear sensor 10. In general, the channel 150 provides the "split" of the split-beam flexure 115, whereby the split-beam flexure 115 may be regarded as a single cantilever beam that is split into a first beam 130 and a second beam 140. In the illustrative embodiment of FIGS. 1 and 3, the channel 150 includes a first rounded portion 155a, a second rounded portion 155b, and a slit portion 152 longitudinally interposed between the first rounded portion 155a and the second rounded portion 155b. In example embodiments, the rounded portions 155a and 155b may be shaped as a square, rectangle, circle, or an oval, for example.

When a wall shear is applied across the head surface 125 of the sensing head 120, the floating element 100 sways in a sway direction parallel to a second transverse axis 40 that is perpendicular to the first transverse axis 30. As used herein, the term "transverse axis" refers to any axis perpendicular to the longitudinal axis 20 of the floating element 100. As will be described subsequently in greater detail, at least one strain gauge 160a, 160b, 160c, 160d or network of multiple strain gauges is coupled to the split-beam flexure 115. When a wall shear is applied across the head surface 125 of the sensing head 120, the strain gauges 160a, 160b, 160c, 160d measure strains imposed on the respective portions of the split-beam flexure 115 to which they are mounted.

In multiple embodiments, the channel 150 of the split-beam flexure 115, or each channel of the split-beam flexure 115 when more than one channel is present, may have a variety of shapes and sizes. The shape of the channel 150 imparts regions or zones of increased strain on the walls of the split-beam flexure 115 when a wall shear is applied across the head surface 125. For example, where the channel 150 is widest, the first beam 130 and the second beam 140 are narrowest. When a wall shear is applied across the head surface 125, strain concentrates in the first beam 130 and the second beam 140 adjacent to where the channel 150 is widest. In one particular example, as shown in FIG. 1, where the channel 150 is widest, thin-wall portions 162a, 162b, 162c, 162d of the split-beam flexure 115 are present in the first beam 130 and the second beam 140. When a wall shear is applied across the head surface 125 of the sensing head 120, strain is concentrated in the thin-wall portions 162a, 162b, 162c, 162d of the split-beam flexure 115. In some embodiments, the split-beam flexure 115 may have a longitudinal plane of symmetry parallel to the first transverse axis 30 through the center of the channel 150.

Figure 4A:
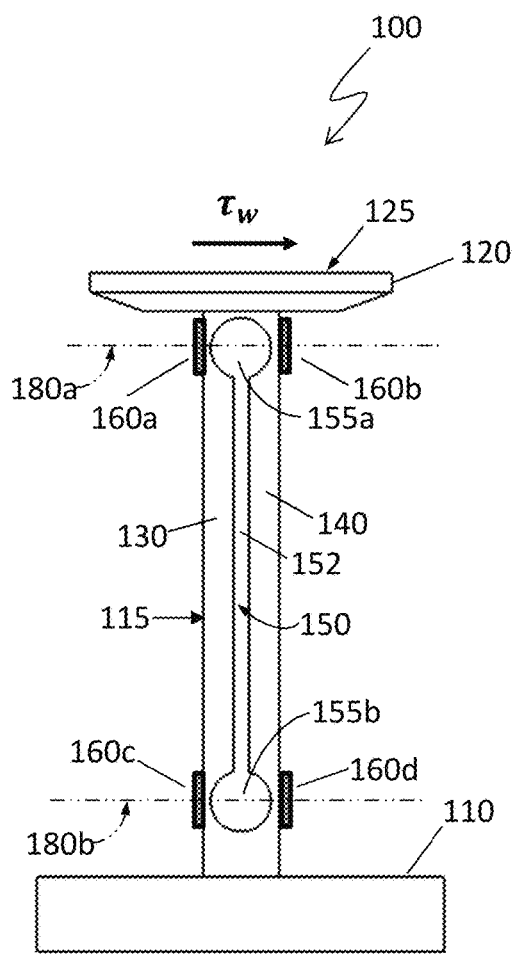
FIG. 4A is a side-view of a floating element of a wall shear sensor according to one or more embodiments described herein.
Figure 4B:
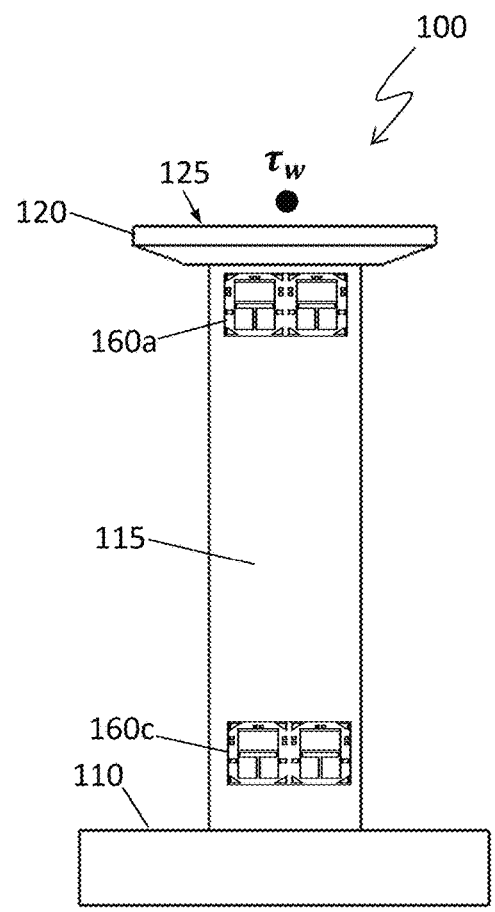
FIG. 4B is a front-view of the floating element of FIG. 4A.

In some embodiments, the strain gauges 160a, 160b, 160c, 160d may be mounted on the split-beam flexure 115 where the strains on the first beam 130 and the second beam 140 are at least significantly greater than the average strain over the split-beam flexure 115 or, preferably, where the strain is the maximum over the split-beam flexure 115. In the illustrative embodiment of FIG. 1, for example, a strain gauge 160a is mounted on the first beam 130 over a thin-wall portion 162a, a strain gauge 160b is mounted on the second beam 140 over a thin-wall portion 162b, a strain gauge 160c is mounted on the first beam 130 over a thin-wall portion 162c, and a strain gauge 160d is mounted on the second beam 140 over a thin-wall portion 162d. As shown in FIG. 4, the split-beam flexure 115 may have one or more maximum strain position 180a, 180b. When the strain gauges 160a, 160b, 160c, 160d are mounted as shown in FIGS. 1 and 4, where strain is increased or maximized, the electrical signals from the strain gauges 160a, 160b, 160c, 160d are more intense, thereby increasing the sensitivity and responsiveness of the wall shear sensor 10 to the wall shear applied across the head surface 125.

In some embodiments of the wall shear sensor 10 the split-beam flexure 115 includes at least one thin-wall portion 162a, 162b, 162c, 162d laterally adjacent to the channel 150. In such embodiments, at least one strain gauge 160a, 160b, 160c, 160d is mounted to the thin-wall portion 162a, 162b, 162c, 162d of the split-beam flexure 115. In further example embodiments, pairs of strain gauges (such as 160a and 160b, or 160c and 160d, for example) may be mounted on thin-wall portions (such as 162a and 162b or 162c and 162d, for example) of the split-beam flexure 115. In such embodiments, a first strain gauge (160a or 160c, for example) of each pair may be mounted on a first side of the split-beam flexure 115, and a second strain gauge (160b or 160d, for example) of each pair may be mounted on a second side of the split-beam flexure 115 opposite the first side. In other embodiments, as in FIG. 5D, pairs of strain gauges (such as 160a and 160b, or 160c and 160d, for example) may be mounted on thin-wall portions of the split-beam flexure 115, a first strain gauge (160a or 160d, for example) of each pair being mounted outside the channel 150, and a second strain gauge (160b or 160c, for example) of each pair being mounted inside the channel 150. In some embodiments, the wall shear sensor 10, includes strain gauges 160c, 160d on the thin-wall portions 162c, 162d split-beam flexure 115 farthest away from the sensing head 120 and optionally may include strain gauges 160a, 160b on the thin-wall portions 162a, 162b nearer the sensing head 120.

As described previously, the channel 150 of the split-beam flexure 115 may vary in shape or size. Examples suitable shapes and sizes for the channel 150 of the split-beam flexure 115 include the embodiments of FIGS. 5A-5E. In each of FIGS. 5A-5E, the sensing head 120 of the floating element 100 has been omitted. Nevertheless, it should be understood that the split-beam flexure 115 in the embodiments of FIGS. 5A-5E, when incorporated in a wall shear sensor, will be subjected to lateral shear forces across a top portion of the split-beam fixture 115 opposite the base 110.

In the embodiment of FIG. 5A, the channel 150 of the split-beam flexure 115 includes a first rounded portion 155a and a second rounded portion 155b that are configured as an "8-shaped hole" (i.e., in the shape of the Arabic number eight). Four strain gauges 160a, 160b, 160c, 160d are mounted on the split-beam flexure adjacent to thin-wall portions where the channel 150 is the widest.

In the embodiment of FIG. 5B, the channel 150 of the split-beam flexure 115 has a "binocular" configuration including a first rounded portion 155a, a second rounded portion 155b, and a slit portion 152 longitudinally interposed between the first rounded portion 155a and the second rounded portion 155b. In various embodiments, the slit portion 152 may be narrower than the diameter of the first rounded portion 155a, the diameter of the second rounded portion 155b, or both. The split-beam flexure includes a first thin-wall portion adjacent to the first rounded portion 155a of the channel 150 and a second thin-wall portion adjacent to the second rounded portion 155b of the channel 150. Four strain gauges 160a, 160b, 160c, 160d are mounted on the split-beam flexure adjacent to thin-wall portions where the channel 150 is the widest.

In the embodiment of FIG. 5C, the channel 150 of the split-beam flexure 115 is a single circular hole. Four strain gauges 160a, 160b, 160c, 160d are located at or adjacent to the thin wall portions where the channel 150 is the widest.

In the embodiment of FIG. 5D, the channel 150 of the split-beam flexure 115 is a single hole shaped as a rectangle with rounded corners. Four strain gauges 160a, 160b, 160c, 160d are located at or adjacent to the thin wall portions where the channel 150 is the widest and where strain is expected to be the most concentrated. Unlike in the embodiments of FIGS. 5A-5C, however, two pairs of strain gauges are arranged such that one strain gauge is outside the channel 150 and the other strain gauge is inside the channel 150.

In the embodiment of FIG. 5E, the split-beam flexure 115 includes a first channel 150a and a second channel 150b, both of which are circular holes. Thereby, the split-beam flexure 115 includes a first beam 130, a second beam 140, and also a third beam 141 between the first channel 150a and the second channel 150b. Four strain gauges 160a, 160b, 160c, 160d are located at or adjacent to the thin wall portions where the first channel 150a and the second channel 150b are their widest and where strain is expected to be the most concentrated.

The strain gauges 160a, 160b, 160c, 160d may be any passive or active electronic device capable of producing an electric signal proportional to an amount of strain present at the surface to which the strain gauge is mounted or attached. The strain gauges 160a, 160b, 160c, 160d are adapted to produce an electrical signal when the head surface 125 of the floating element 100 is exposed to wall shear. The electrical signal arises from the resulting force or moment experienced by the head surface 125. When the floating element 100 laterally deflects or sways, the electrical signal produced from the one or more strain gauges 160a, 160b, 160c, 160d may be interpreted to determine the wall shear. In some embodiments, the electrical signal is a change in the electrical resistance of the one or more strain gauges 160a, 160b, 160c, 160d that is measurable with a Wheatstone bridge. As the split-beam flexure 115 bends or sways, the one or more strain gauges 160a, 160b, 160c, 160d mounted to the split-beam flexure 115 are deformed, thereby resulting in the change in electrical resistance. It should be understood that interpretation of the electrical signals may require an initial empirical calibration of the wall shear sensor 10, whereby determination of the applied force requires a correlation of an actual measurement to the empirical calibration. In non-limiting examples, the strain gauges 160a, 160b, 160c, 160d may include semiconductor strain gauges, foil strain gauges, piezoelectric elements, piezoresistive elements, microelectromechanical (MEM) devices, capacitors, or combinations thereof. The strain gauges 160a, 160b, 160c, 160d may be configured in one or more Wheatstone bridges or may be configured in quarter-bridge, half-bridge, or full-bridge arrangements with dummy resistors, depending on the number of strain gauges present.

Materials used in the floating element 100 and the split-beam flexure 115 may include conventional transducer spring element materials that are constructed from or include, for example, 20XX/60XX/70XX aluminum alloys, BeCu, 6Al4V titanium, 410/63X/S15500 stainless steel, and other durable alloys or combinations thereof. In some non-limiting examples, the floating element 100 and the split-beam flexure 115 also be made from lighter magnesium alloys, ceramics, or plastics, for example. However, it should be understood that the floating element 100 and the split-beam flexure 115 may include or be made from materials substantially different than those listed, provided the wall shear sensor 10 operates according to the same general principles described in the embodiments of this disclosure.

The wall shear sensor 10 may further include a sensor housing 200 that laterally surrounds the floating element 100. Thereby, an interior space 210 laterally surrounding the floating element 100 is defined between the floating element 100 and the sensor housing 200. The interior space 210 includes a small gap portion 220 laterally surrounding the sensing head 120 of the floating element 100. The small gap portion 220 is sufficiently wide to provide freedom for the floating element 100 to laterally deflect or "float" as a result of wall shear that is applied across the head surface 125. The small gap portion 220 is sufficiently narrow to avoid unwanted flow interference across the head surface 125. The head surface 125 of the sensing head 120 is exposed outside the sensor housing 200. Thus, the head surface 125 may be directly in contact with wall shear across the flow surface 350 of a test body 300 (FIG. 2).

The wall shear sensor 10 according to the embodiments previously described may be incorporated into a wall shear measurement system. Referring to FIGS. 1-3, a wall shear measurement system 400 may include a test body 300 having a flow surface 350. The wall shear measurement system 400 may further include at least one sensor housing 200 mounted to the test body 300 and a wall shear sensor 10, as previously described, in the at least one sensor housing 200.

For example, the wall shear sensor 10 of the wall shear measurement system 400 may include a floating element 100 fixedly attached to a base 110, the floating element 100 having a sensing head 120 opposite the base 110, and a split-beam flexure 115 between the sensing head 120 and the base 110. The wall shear sensor 10 may further include at least one strain gauge 160a, 160b, 160c, 160d coupled to the split-beam flexure 115 that measures a strain imposed on the split-beam flexure 115 when a wall shear is applied across the head surface 125 of the sensing head 120.

In the wall shear sensor 10 of the wall shear measurement system 400, the split-beam flexure 115 has a channel 150 defined through the split-beam flexure 115 parallel to a first transverse axis 30 of the split-beam flexure 115. When a wall shear is applied across the head surface 125 of the sensing head 120, the wall shear sensor 10 sways or pivots in a sway direction parallel to a second transverse axis 40 or the floating element 100 that is perpendicular to the first transverse axis 30. The sensor housing 200 laterally surrounds the floating element 100, such that an interior space 210 laterally surrounding the floating element 100 is defined between the floating element 100 and the sensor housing 200. The interior space 210 includes a small gap portion 220 laterally surrounding the sensing head 120 of the floating element 100. The head surface 125 of the sensing head 120 is exposed outside the sensor housing 200. In some embodiments of the wall shear measurement system 400, the head surface 125 of the sensing head 120 of the wall shear sensor 10 is coplanar with the flow surface 350 of the test body 300.

Figure 6:
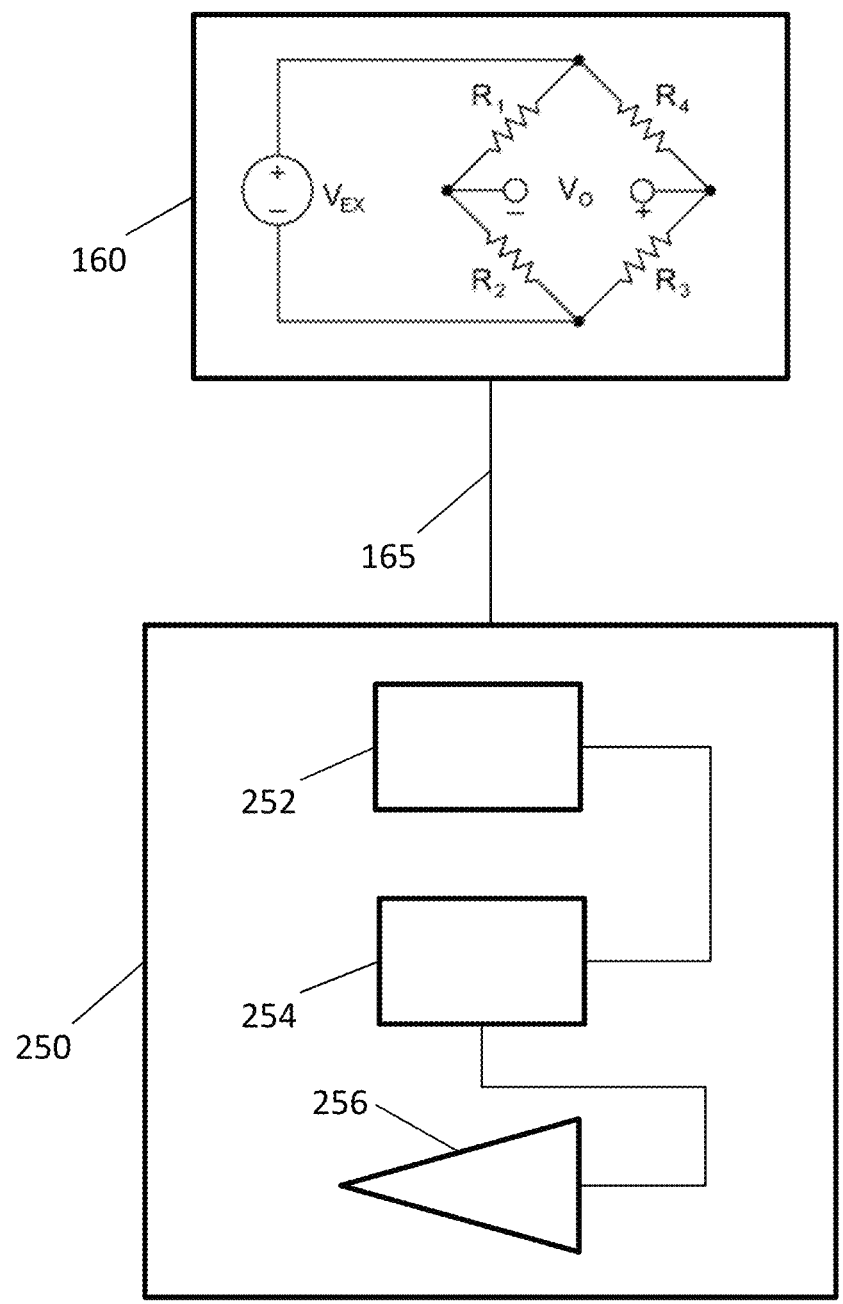
FIG. 6 is a schematic diagram of a data acquisition system of a wall shear measurement system comprising a wall shear sensor according to one or more embodiments described herein.

Referring to FIG. 6, the wall shear measurement system 400 may further include a data acquisition system 250 communicatively coupled to the strain gauges 160 of the wall shear sensor 10 through a communication path 165. The data acquisition system 250 may include at least one of a memory module 252, a processor 254, a signal conditioner 256, or a combination thereof. These components may be arranged in a circuit in any order to achieve a desired result or function. Thus, it should be understood that the schematic of the data acquisition system 250 is not intended to limit the ordering or interconnection of the components to a specific configuration. The communication path 165 may include conductive wires, conductive traces, optical waveguides, or a combination thereof. The strain gauges 160 may be chosen from semiconductor strain gauges, foil strain gauges, piezoelectric elements, piezoresistive elements, microelectromechanical (MEM) devices, or capacitors for example, and may be configured in one or more Wheatstone bridges or may be configured in quarter-bridge, half-bridge, or full-bridge arrangements with dummy resistors, depending on the number of strain gauges present.

In some embodiments, the wall shear measurement system 400 may include a plurality of wall shear sensors, each wall shear sensor being disposed within a respective sensor housing mounted to the test body. The plurality of wall shear sensors in such embodiments may be networked in a manner that enables simultaneous data acquisition and interpretation from each of the individual wall shear sensors.

Still referring to FIG. 6, electrical signals generated at the strain gauges 160 may be processed by a data acquisition system 250 having at least one memory module 252, at least one processor 254, and/or one or more signal conditioners 256. Each of these components may be connected to the strain gauges 160 through a communication path 165. The at least one processor 254 may be any device capable of executing machine readable instructions. For example, the at least one processor 254 may be a controller, an integrated circuit, a microchip, a computer, or any other computing device. The at least one processor 254 may be communicatively coupled to a communication path 165 that provides signal interconnectivity between various components of the wall shear sensor 10. Thus, the communication path 165 may communicatively couple any number of processors with one another and may allow the various components coupled to the communication path 165 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, for example. The signal conditioner 256 may include any electronic device capable of providing filtering, amplifying, electrical isolation, excitation, linearization, cold junction compensation, or attenuation, for example.

Moreover, the communication path 165 may be formed from any medium that is capable of transmitting a signal such as, for example, conductive wires, conductive traces, optical waveguides, or the like. In some embodiments, the communication path 165 may facilitate the transmission of wireless signals, such as WiFi, Bluetooth, and the like. Moreover, the communication path 165 may be formed from a combination of media capable of transmitting signals. In one embodiment, the communication path 165 may include a combination of conductive traces, conductive wires, connectors, and buses that cooperate to permit the transmission of electrical data signals to components such as processors, memories, sensors, input devices, output devices, and communication devices. Accordingly, the communication path 165 may include a vehicle bus, such as for example a LIN bus, a CAN bus, a VAN bus, or the like. Additionally, it is noted that the term "signal" may include a waveform (for example, electrical, optical, magnetic, mechanical or electromagnetic), such as DC, AC, sinusoidal-wave, triangular-wave, square-wave, vibration, and the like, capable of traveling through a medium.

The wall shear sensor 10 of the wall shear measurement system 400 may further include at least one memory module 252 coupled to the communication path 165. The at least one memory module 252 may include RAM, ROM, flash memories, hard drives, or any device capable of storing machine readable instructions such that the machine readable instructions can be accessed by the at least one processor 254. The machine readable instructions may include logic or algorithm(s) written in any programming language of any generation (e.g., 1GL, 2GL, 3GL, 4GL, or 5GL) such as, for example, machine language that may be directly executed by the at least one processor 254, or assembly language, object-oriented programming (OOP), scripting languages, microcode, etc., that may be compiled or assembled into machine readable instructions and stored on the at least one memory module 252. Alternatively, the machine readable instructions may be written in a hardware description language (HDL), such as logic implemented via either a field-programmable gate array (FPGA) configuration or an application-specific integrated circuit (ASIC), or their equivalents. The signal conditioner 256 may be configured to filter the signal, isolate possible sources of signal perturbations, and amplify the power of an electrical signal produced by the strain gauges 160. In some embodiments, the data acquisition system 250 may not include a separate signal conditioner 256 where at least one processor 254 is programmed to condition the signal obtained from the strain gauges 160. In some embodiments, additional electronic packages may be used in place of, or in conjunction with a signal conditioner 256 to boost the signal level, increase measurement resolution and improve signal-to-noise ratios.

When the wall shear measurement system 400 according to embodiments of this disclosure are implemented in applications such as measuring wall shear on a test body, a relevant concern is an induced moment across the head surface 125 due to the effect of pressure gradients or shock wave impingements on the accuracy and reliability of measurements. In practice, when a wall shear sensor 10 is subjected to flows across the head surface 125 of the sensing head 120, pressure gradients or other transient events may arise that cause unequal downward forces at different points of the sensing head 120. In turn, the unequal downward forces may result in a moment on the sensing head 120. In single-beam or cantilever wall shear sensors that lack a channel or multiple beams, such a moment on the sensing head may severely decrease the ability of the single-beam wall shear sensor to measure actual wall shear, because the wall shear cannot be decoupled from the induced moment. It is believed that the ability of the wall shear sensor 10 according to embodiments of this disclosure to mechanically isolate the primary wall shear measurement from a pressure gradient or shock wave induced moment may depend at least in part on the separation of measured flexure strain between the strain gauges 160*a*, 160*b*, 160*c*, 160*d*. Generally, a wall shear acts as a point load at the sensing head 120 while a pressure gradient or shock wave interaction acts as a moment at the sensing head 120. The contribution from each component has a unique strain distribution pattern throughout the split-beam flexure 115. It is believed that through mechanical design, the split-beam flexure 115 can nearly isolate the tip point load influence for measurement while greatly reducing the influence of the tip moment contribution.

A wall shear sensor 10 according to the embodiment of FIG. 1 was modeled using Finite Element Analysis (FEA) to assess both the sensitivity of the wall shear sensor to small-magnitude wall shear and the ability of the wall shear sensor 10 to mechanically isolate wall shear from the influence of a pressure gradient or shock wave induced moments. As a comparative example, a single-beam wall shear sensor was modeled in the same manner. The modeled single-beam wall shear sensor had the same geometric configuration as the wall shear sensor 10 according to the embodiment of FIG. 1, except that the flexure of the single-beam wall shear sensor did not include a channel 150. The results obtained from these models will now be described with reference to FIGS. 7A-10B.

Equivalent Von Mises strain models were generated for a split-beam flexure 115 of a floating element 100 according to the embodiment of FIG. 3 and of a single-beam flexure 515 of a comparative floating element 500 having the same size and shape as the split-beam flexure 115. The models were simulated with the material properties of aluminum alloy 2024 for both the split-beam flexure 115 and the single-beam flexure 515. The models simulated a wall shear ($\tau_w$) of 250 Pa applied across the sensing heads the floating elements in the primary sway direction of the flexures (perpendicular to the channel 150 in the case of the split-beam flexure 115).

Figure 7A:
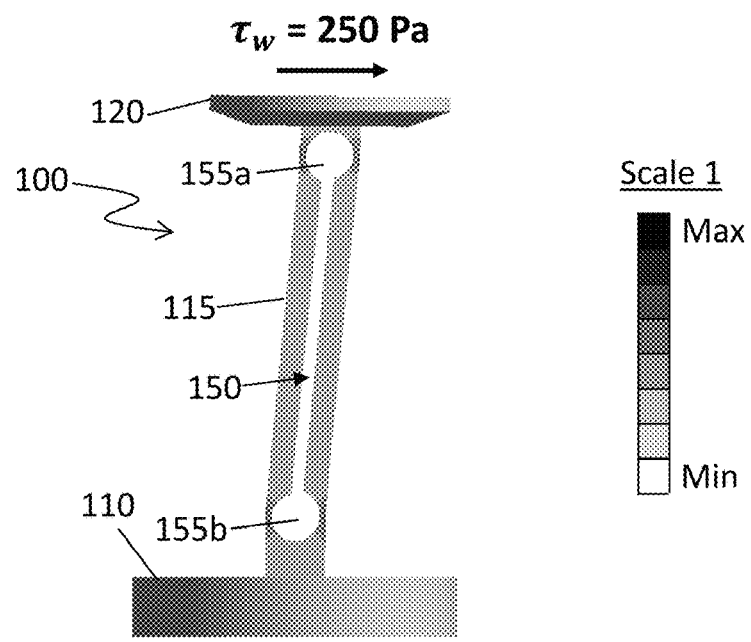
FIG. 7A is a simulated side-view strain diagram of a wall shear sensor according to an embodiment described herein when a wall shear is applied across the head surface of the wall shear sensor.
Figure 7B:
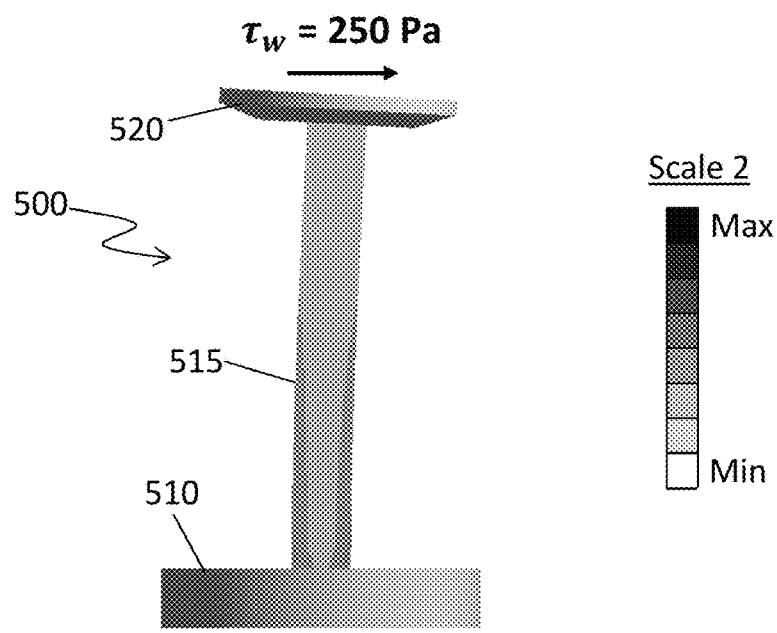
FIG. 7B is a simulated side-view strain diagram of a comparative single-beam or cantilever wall shear sensor lacking a channel when a wall shear is applied across the head surface of the single-beam wall shear sensor.
Figure 8A:
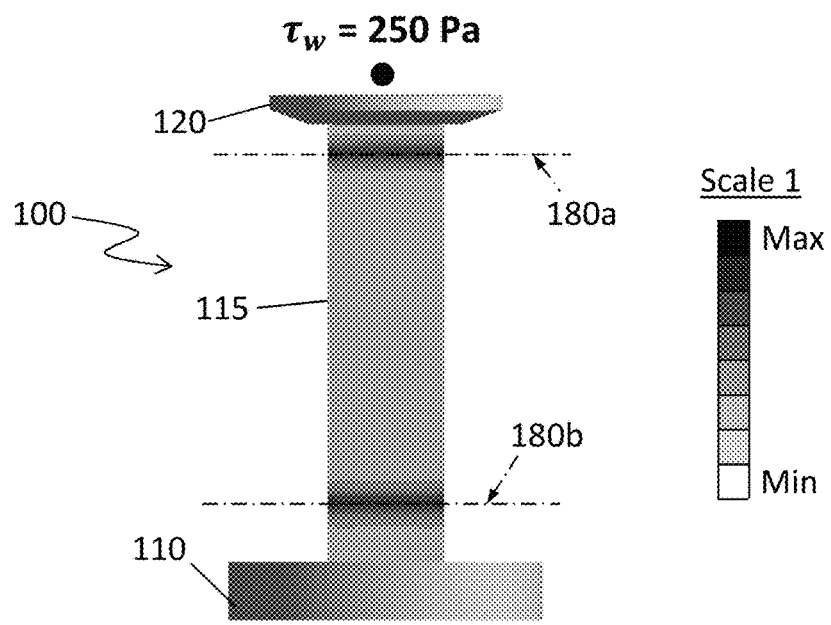
FIG. 8A is a simulated front-view strain diagram of the wall shear sensor of FIG. 7A when a wall shear is applied across the head surface of the wall shear sensor.
Figure 8B:
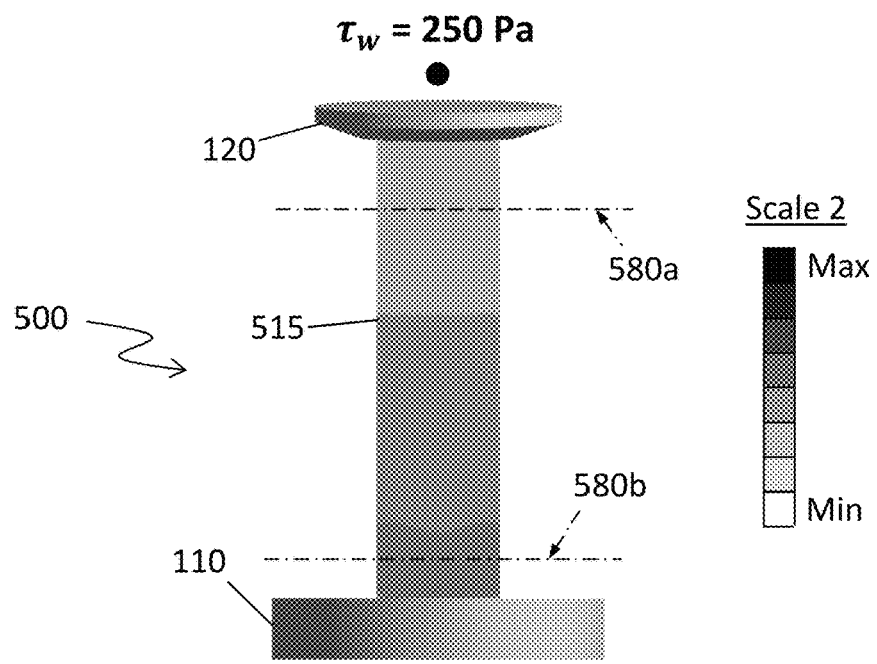
FIG. 8B is a simulated front-view strain diagram of the comparative single-beam or cantilever wall shear sensor of FIG. 7B when a wall shear is applied across the head surface of the single-beam wall shear sensor.
Figure 9A:
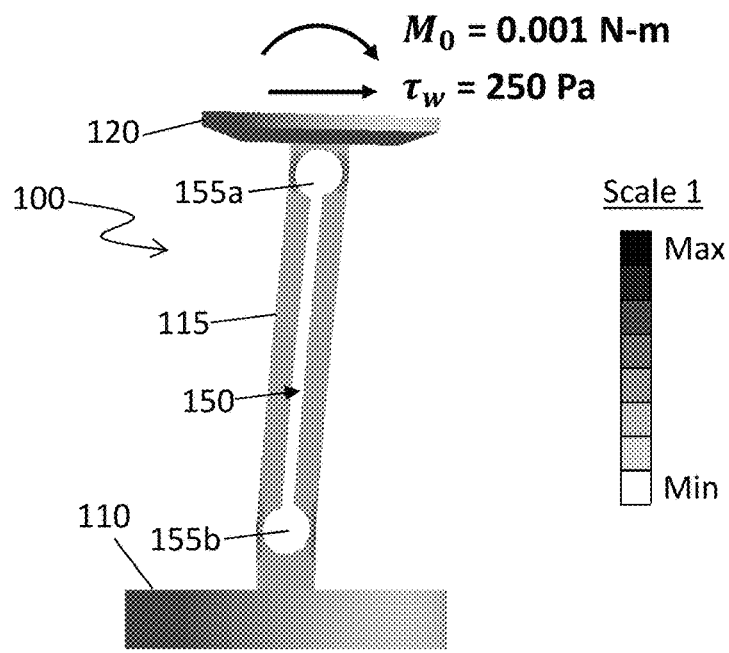
FIG. 9A is a simulated side-view strain diagram of a wall shear sensor according to an embodiment described herein when both a wall shear and a pressure gradient or shock wave induced moment are applied across the head surface of the wall shear sensor.
Figure 9B:
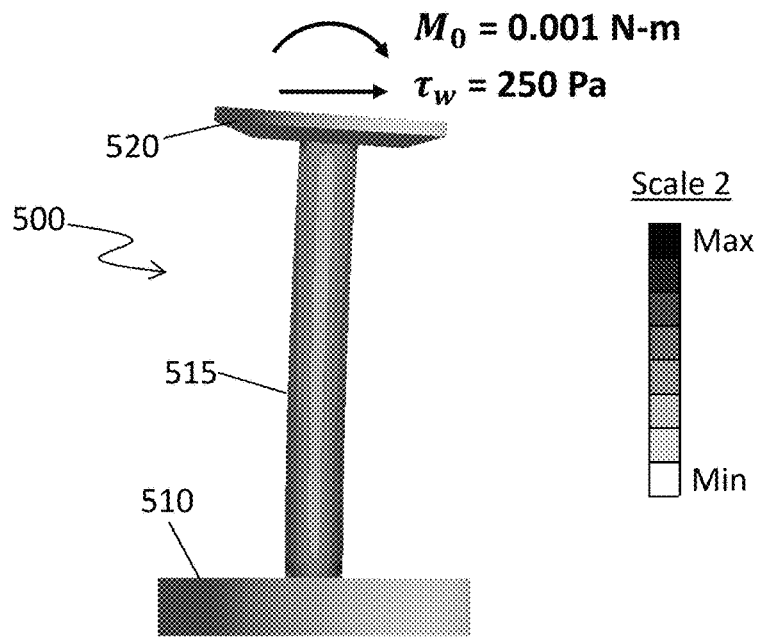
FIG. 9B is a simulated side-view strain diagram of a comparative single-beam or cantilever wall shear sensor lacking a channel when both a wall shear and a pressure gradient or shock wave induced moment are applied across the head surface of the single-beam wall shear sensor.
Figure 10A:
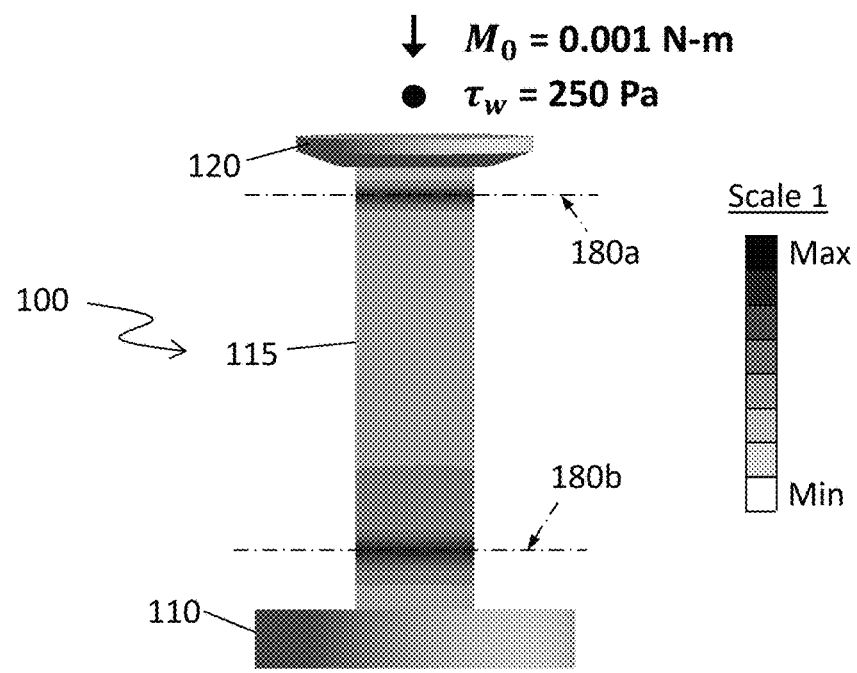
FIG. 10A is a simulated front-view strain diagram of the wall shear sensor of FIG. 9A both a wall shear and a pressure gradient or shock wave induced moment are applied across the head surface of the wall shear sensor.
Figure 10B:
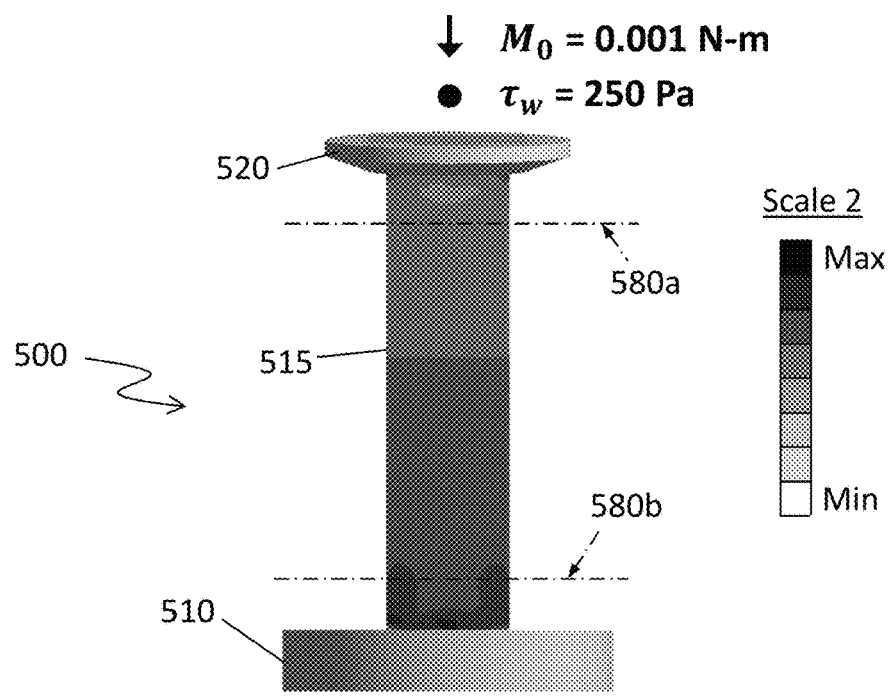
FIG. 10B is a simulated front-view strain diagram of a comparative single-beam or cantilever wall shear sensor of FIG. 9B when both a wall shear and pressure gradient or shock wave induced moment are applied across the head surface of the single-beam wall shear sensor.

The strain diagram of the side-view of the floating element 100 having a split-beam flexure 115 is provided in FIG. 7A, and the strain diagram of the side-view of the comparative floating element 500 having a single-beam flexure 515 is provided in FIG. 7B. In the split-beam flexure 115 (FIG. 7A), strain is concentrated at the first rounded portion 155*a* and the second rounded portion 155b of the channel 150, where thin-wall portions of the split-beam flexure 115 are present. In contrast, in the single-beam flexure 515, strain gradually increases from the sensing head 520 down to the base 510 as is consistent with elementary beam theory. These differences are particularly evident in the front-views of FIG. 8A (split-beam flexure 115) and FIG. 8B (single-beam flexure 515). In FIG. 8A, the maximum-strain positions 180a, 180b of the single-beam flexure 515 align with the thin-wall portions adjacent to the first rounded portion 155a and the second rounded portion 155b of the channel 150. For comparison purposes, comparative reference positions 580a, 580b in FIG. 8B show the positions on the single-beam flexure 515 where maximum strain would be present on the split-beam flexure 115 of FIG. 8A.

As part of the strain modeling, numerical values of strain at the maximum-strain positions 180a, 180b of the split-beam flexure 115 and at the comparative reference positions 580a, 580b of the single-beam flexure 515 were computed. For the split-beam flexure 115, at the upper maximum-strain position 180a, strain was 17.1με, and at the lower maximum-strain position 180b, strain was 17.3με. For the single-beam flexure 515, at the upper comparative reference position 580a, strain was 0.14με, and at the lower comparative reference position 580b, strain was 0.88με. Thus, comparing the strain values from the lower positions (17.3με vs. 0.88με), the split-beam flexure 115 exhibits a strain output approximately 20 times that of the single-beam flexure 515. In practice, the increased strain output translates to greater sensitivity, higher signal-to-noise ratio, and more reliable performance.

An additional model was computed for the split-beam flexure 115 and the single-beam flexure 515 to assess the effect of a moment induced from a pressure gradient or shock wave. The simulation provided to each flexure a wall shear ($\tau_w$) of 250 Pa and a moment ($M_0$) of 0.001 N·m across the sensing heads the floating elements in the primary sway direction of the flexures (perpendicular to the channel 150 in the case of the split-beam flexure 115). The simulated strain diagram of the side-view of the floating element 100 having a split-beam flexure 115 is provided in FIG. 9A, and the strain diagram of the side of the comparative floating element 500 having a single-beam flexure 515 is provided in FIG. 9B.

For the simulation including both the wall shear and moment, again the numerical values of strain at the maximum-strain positions 180a, 180b of the split-beam flexure 115 and at the comparative reference positions 580a, 580b of the single-beam flexure 515 were computed. These differences are particularly evident in the front-views of FIG. 10A (split-beam flexure 115) and FIG. 10B (single-beam flexure 515). For the split-beam flexure 115, at the upper maximum-strain position 180a, strain was 17.1με, and at the lower maximum-strain position 180b, strain was 17.5με. For the single-beam flexure 515, at the upper comparative reference position 580a, strain was 1.31με, and at the lower comparative reference position 580b, strain was 2.14με.

To assess the errors to simulated wall shear measurements arising from the influence of the pressure gradient or shock wave induced moment, it was assumed that total strain arising from wall shear and moment combined are additive and only the lower positions on the respective flexures were considered. For the split-beam flexure 115, the strain at the lower maximum-strain position 180b under wall shear only was 17.3με. This value increased by 0.2με to 17.5με when the pressure gradient or shock wave induced moment was present. Thus, the error caused by the moment in the split-beam flexure 115 was 0.2/17.3 or about 1.2%. For the single-beam flexure 515, the strain at the lower comparative reference position 580b under wall shear only was 0.88με. This value increased by 1.26με to 2.14με when the pressure gradient or shock wave induced moment was present. Thus, the error caused by the moment in the single-beam flexure 515 was 1.26/0.88 or about 143%. Compared to the single-beam flexure 515, the split-beam flexure 115 is significantly less prone to errors in wall shear measurements that would arise from the presence of a pressure gradient or shock wave impingement.

As demonstrated through the example simulations, the split-beam flexure 115 of a floating element 100 according to the embodiment has a much greater sensitivity to wall shear (20×) over the comparative floating element 500 having a single-beam flexure 515, while minimizing the error caused by the pressure gradient or shock wave impingement to 1.2% compared to 143%. It follows that wall shear sensors 10 and wall shear measurement systems 400 according to embodiments of this disclosure are capable of directly measuring skin friction drag in a manner that is highly sensitive, yet with significant reduction or elimination of errors resulting from the moment of forces caused by impinging pressure gradients or shock waves.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that terms like "preferably," "commonly," and "typically" are not utilized herein to limit the scope of the appended claims or to imply that certain features are critical, essential, or even important to the structure or function of the claimed subject matter. Rather, these terms are merely intended to highlight alternative or additional features that may or may not be utilized in a particular embodiment.

What is claimed is:

1. A wall shear sensor comprising:
   a floating element fixedly attached to a base, the floating element having a sensing head opposite the base, and a split-beam flexure between the sensing head and the base, a longitudinal axis of the floating element being defined perpendicular to the base; and
   at least one strain gauge coupled to the split-beam flexure that measures a strain imposed on a portion of the split-beam flexure when a wall shear is applied across a head surface of the sensing head;
   wherein:
   the split-beam flexure comprises a single cantilever beam split into a first beam and a second beam by has at least one channel defined through the split-beam flexure parallel to a first transverse axis of the floating element, the first transverse axis being perpendicular to the longitudinal axis;
   the floating element sways in a sway direction parallel to a second transverse axis that is perpendicular to both the first transverse axis and the longitudinal axis of the floating element when the wall shear is applied; and
   the wall shear sensor mechanically isolates measurement of the wall shear by the at least one strain gauge from moments induced on the sensing head by impinging pressure gradients or shock waves.

2. The wall shear sensor of claim 1, wherein the split-beam flexure comprises at least one thin-wall portion adjacent to the channel.

3. The wall shear sensor of claim 2, wherein at least one strain gauge is mounted to the thin-wall portion of the split-beam flexure.

4. The wall shear sensor of claim 2, wherein pairs of strain gauges are mounted on thin-wall portions of the split-beam flexure, a first strain gauge of each pair being mounted on a first side of the split-beam flexure, a second strain gauge of each pair being mounted on a second side of the split-beam flexure opposite the first side.

5. The wall shear sensor of claim 2, wherein pairs of strain gauges are mounted on thin-wall portions of the split-beam flexure, a first strain gauge of each pair being mounted outside the channel, a second strain gauge of each pair being mounted inside the channel.

6. The wall shear sensor of claim 1, wherein the channel comprises a first rounded portion and a second rounded portion.

7. The wall shear sensor of claim 6, wherein the first round portion and the second rounded portion are configured as an 8-shaped hole.

8. The wall shear sensor of claim 6, wherein:
the channel further comprises a slit portion longitudinally interposed between the first rounded portion and the second rounded portion; and
the slit portion is narrower than the diameter of the first rounded portion, the diameter of the second rounded portion, or both.

9. The wall shear sensor of claim 6, wherein:
the channel further comprises a slit portion longitudinally interposed between the first rounded portion and the second rounded portion; and
the split-beam flexure comprises a first thin-wall portion adjacent to the first rounded portion of the channel and a second thin-wall portion adjacent to the second rounded portion of the channel.

10. The wall shear sensor of claim 9, wherein at least one pair of strain gauges is mounted to the first thin-wall portion and at least one pair of strain gauges is mounted to the second thin-wall portion.

11. The wall shear sensor of claim 1, wherein the strain gauges are chosen from semiconductor strain gauges, foil strain gauges, piezoelectric elements, piezoresistive elements, microelectromechanical (MEM) devices, capacitors, or combinations thereof.

12. The wall shear sensor of claim 1, wherein the split-beam flexure comprises at least two channels defined through the split-beam flexure parallel to a transverse axis of the split-beam flexure.

13. The wall shear sensor of claim 1, wherein:
the wall shear sensor further comprises a sensor housing that laterally surrounds the floating element;
an interior space laterally surrounding the floating element is defined between the floating element and the sensor housing;
the interior space comprises a small gap portion laterally surrounding the sensing head of the floating element; and
the head surface of the sensing head is exposed outside the sensor housing.

14. A wall shear measurement system comprising:
a test body having a flow surface;
at least one sensor housing mounted to the test body; and
a wall shear sensor in the at least one sensor housing, the wall shear sensor comprising:
a floating element fixedly attached to a base, the floating element having a sensing head opposite the base, and a split-beam flexure between the sensing head and the base, a longitudinal axis of the floating element being defined perpendicular to the base; and
at least one strain gauge coupled to the split-beam flexure that measures a strain imposed on the split-beam flexure when a wall shear is applied across a head surface of the sensing head,
wherein:
the split-beam flexure comprises a single cantilever beam split into a first beam and a second beam by at least one channel defined through the split-beam flexure parallel to a first transverse axis of the floating element, the first transverse axis being perpendicular to the longitudinal axis;
the wall shear sensor sways in a sway direction parallel to a second transverse axis that is perpendicular to both the transverse axis and the longitudinal axis of the floating element when the wall shear is applied;
the wall shear sensor mechanically isolates measurement of the wall shear by the at least one strain gauge from moments induced on the sensing head by impinging pressure gradients or shock waves;
the sensor housing laterally surrounds the floating element of the wall shear sensor;
an interior space laterally surrounding the floating element is defined between the floating element and the sensor housing;
the interior space comprises a small gap portion laterally surrounding the sensing head of the floating element; and
the head surface of the sensing head is exposed outside the sensor housing.

15. The wall shear measurement system of claim 14, wherein the head surface of the sensing head is coplanar with the flow surface.

16. The wall shear measurement system of claim 14, further comprising a data acquisition system communicatively coupled to the strain gauges of the wall shear sensor through a communication path.

17. The wall shear measurement system of claim 16, wherein the data acquisition system comprises at least one of a memory module, a processor, a signal conditioner, or a combination thereof.

18. The wall shear measurement system of claim 16, wherein the communication path comprises conductive wires, conductive traces, optical waveguides, or a combination thereof.

19. The wall shear measurement system of claim 14, wherein the strain gauges are chosen from semiconductor strain gauges, foil strain gauges, piezoelectric elements, piezoresistive elements, microelectromechanical (MEM) devices, capacitors, or combinations thereof.

20. The wall shear measurement system of claim 14, comprising a plurality of wall shear sensors, each wall shear sensor being disposed within a respective sensor housing mounted to the test body.

* * * * *